(12) United States Patent
Jaffe

(10) Patent No.: US 9,855,010 B2
(45) Date of Patent: Jan. 2, 2018

(54) MAINSTREAM GAS ANALYZER CONFIGURABLE TO REMOVABLY COUPLE WITH A SIDESTREAM GAS SAMPLING COMPONENT

(75) Inventor: Michael Brian Jaffe, Cheshire, CT (US)

(73) Assignee: Koninklijke Philips N.V., Eindhoven (NL)

( * ) Notice: Subject to any disclaimer, the term of this patent is extended or adjusted under 35 U.S.C. 154(b) by 618 days.

(21) Appl. No.: 14/113,543

(22) PCT Filed: Apr. 2, 2012

(86) PCT No.: PCT/IB2012/051606
§ 371 (c)(1),
(2), (4) Date: Oct. 23, 2013

(87) PCT Pub. No.: WO2012/146991
PCT Pub. Date: Nov. 1, 2012

(65) Prior Publication Data
US 2014/0052014 A1    Feb. 20, 2014

Related U.S. Application Data

(60) Provisional application No. 61/479,064, filed on Apr. 26, 2011.

(51) Int. Cl.
*A61B 5/097* (2006.01)
*A61B 5/00* (2006.01)
*A61B 5/08* (2006.01)
*G01N 1/22* (2006.01)
*A61M 16/00* (2006.01)

(52) U.S. Cl.
CPC ............ *A61B 5/72* (2013.01); *A61B 5/082* (2013.01); *A61B 5/097* (2013.01); *A61B 5/742* (2013.01); *A61M 16/00* (2013.01); *G01N 1/2247* (2013.01); *F04C 2270/041* (2013.01)

(58) Field of Classification Search
CPC ....... A61M 16/00; G01N 1/2247; A61B 5/08; A61B 5/097
See application file for complete search history.

(56) References Cited

U.S. PATENT DOCUMENTS

| 4,958,075 A | 9/1990 | Mace et al. | |
|---|---|---|---|
| 6,629,934 B2 | 10/2003 | Mault et al. | |
| 6,954,702 B2 * | 10/2005 | Pierry | A61B 5/083 422/94 |
| 7,341,563 B2 * | 3/2008 | Rich | A61B 5/0833 422/84 |
| 7,432,508 B2 * | 10/2008 | Daniels | A61B 5/083 250/343 |
| 7,606,668 B2 | 10/2009 | Pierry et al. | |

(Continued)

FOREIGN PATENT DOCUMENTS

| EP | 2062531 A1 | 5/2009 |
|---|---|---|
| EP | 2275031 A1 | 1/2011 |
| WO | 2008005907 A2 | 1/2008 |

*Primary Examiner* — Jacqueline Cheng
*Assistant Examiner* — Angeline Premraj

(57) ABSTRACT

Systems and methods for analyzing respiratory gas are configured to function in both divertive and non-divertive configurations. A mainstream gas analyzer housing economically and removably couples with a sidestream gas sampling component.

10 Claims, 8 Drawing Sheets

(56) References Cited

U.S. PATENT DOCUMENTS

| | | |
|---|---|---|
| 7,748,280 B2 | 7/2010 | Jaffe et al. |
| 8,282,570 B2 | 10/2012 | Rich et al. |
| 8,796,034 B2 | 8/2014 | von Bahr et al. |
| 2009/0062673 A1 | 3/2009 | Scampoli |
| 2012/0318266 A1* | 12/2012 | Chou .................... A61B 5/087 |
| | | 128/204.23 |
| 2014/0052014 A1 | 2/2014 | Jaffe |

* cited by examiner

MAINSTREAM GAS ANALYZER CONFIGURABLE TO REMOVABLY COUPLE WITH A SIDESTREAM GAS SAMPLING COMPONENT

CROSS-REFERENCE TO PRIOR APPLICATIONS

This application is the U.S. National Phase application under 35 U.S.C. §371 of International application No. PCT/IB2012/051606, filed on Apr. 2, 2012, which claims the benefit of U.S. Provisional Patent Application No. 61/479,064, filed on Apr. 26, 2011. These applications are hereby incorporated by reference herein.

BACKGROUND

1. Field

The present disclosure pertains to a system and method for coupling and controlling a gas analyzer and a (divertive) gas sampling component.

2. Description of the Related Art

It is well known to analyze gas (i.e. constituent gas components in a gas mixture, and/or concentrations of constituent gas components in a gas mixture) in either diverting configurations or non-diverting configurations, in particular for respiratory gas. Both configurations offer benefits, but for economic reasons both configurations may not be available in such clinical environments as an intensive care unit, emergency department, or pre-hospital environment.

SUMMARY

Accordingly, it is an object of one or more embodiments to provide a gas sampling system including a first housing and a second housing, configured to removably couple with each other. The first housing includes a sensor assembly configured to measure a gaseous molecular species in a gas mixture and removably engages an airway adapter configured for insertion into a breathing circuit, wherein the breathing circuit is in fluid communication with a subject. The second housing includes a pump. The first and second housing are further configured to engage a sampling cell such that gas within the sampling cell is measured by the sensor assembly, and such that operation of the pump moves gas through the sampling cell.

It is yet another aspect of one or more embodiments to provide a method of analyzing gas. The method includes removably coupling a first housing including a sensor assembly and a second housing including a pump, wherein the sensor assembly is configured to measure a gaseous molecular species in a gas mixture, wherein the first housing is further configured to removably engage an airway adapter, and wherein the airway adapter is configured for insertion into a breathing circuit configured to provide a pressurized flow of breathable gas to a subject; removably engaging a sampling cell such that gas within the sampling cell can be measured by the sensor assembly of the first housing, and such that operation of the pump moves gas through the sampling cell; and measuring by the sensor assembly a gaseous molecular species in a gas mixture within the sampling cell It is yet another aspect of one or more embodiments to provide a system configured to analyze gas. The system includes means for measuring a gaseous molecular species in a gas mixture; means for housing the means for measuring a gaseous molecular species in a gas mixture, further configured to removably engage an airway adapter, wherein the airway adapter is configured for insertion into a breathing circuit configured to communicate with an airway of a subject; means for housing a pump; means for removably coupling the means for housing a sensor assembly and the means for housing a pump; and means for removably engaging a sampling cell such that gas within the sampling cell is analyzed by the means for measuring a gaseous molecular species in a gas mixture, and such that operation of the pump moves gas through the sampling cell.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the any limitations.

DETAILED DESCRIPTION OF EXEMPLARY EMBODIMENTS

Figure 1:
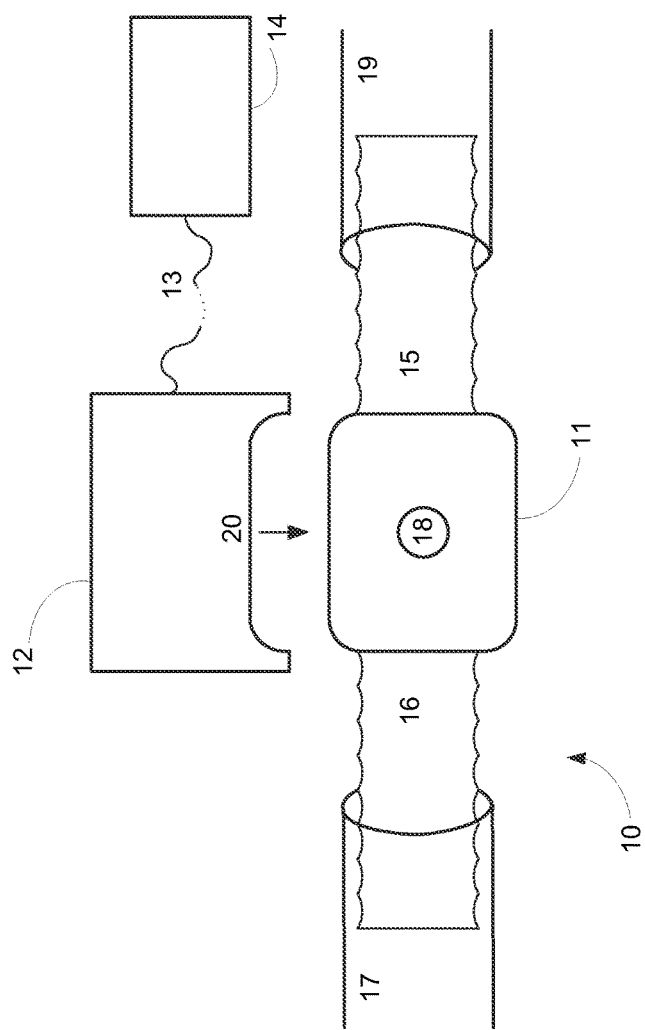
FIG. 1 schematically illustrates the combined use of an airway adapter and a gas analyzer housing.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Gas analyzers may be available in diverting configurations and non-diverting configurations, commonly referred to as sidestream and mainstream. Gas analyzers may have medical applications, for example when being used to measure constituent components of respiratory gas, and/or concentrations of such components in a gas mixture. Typical medical applications may analyze e.g. the oxygen or carbon dioxide concentration in breathable and/or breathed gas/air. In non-diverting configurations a so-called airway adapter may be inserted in the breathing circuit. An airway adapter may include an input segment, and output segment, and an adapter body—coupling the input and output segments—configured to provide an optical path through the airway adapter. A housing including a sensor assembly may be removably coupled with the airway adapter such that the optical path is available for measurements by the sensor assembly. A sensor assembly may include one or more of a source assembly, windows, a detector assembly, and a processing component. The sensor assembly is configured to pass a beam of radiation from the source assembly along the optical path to the detector assembly. The detector assembly, in cooperation with a processing component, may be configured to ascertain the attenuation of energy in the beam of radiation impinging upon a detector in the detector assembly. This attenuation may be proportional to the absorption through the gas by a particular gaseous molecular species in a particular band of wavelengths. This attenuation may thus be suitable for measurements by the sensor assembly of a gaseous molecular species in a gas mixture.

Non-diverting configurations may be used when a subject is using, for example, an endotracheal tube or a mask, whereas diverting configurations may be used, for example, for spontaneously breathing subjects using a nasal/oral cannula. With diverting configurations, a pump may be used to move the gas, via a sampling line, through a sampling cell. The principles of operation of a sensor assembly (using e.g. a source assembly and a detector assembly) may be similar between diverting and non-diverting configurations. Accordingly, a modular approach designed to combine both configurations and thus serve subjects using either breathing interface may be economical.

FIG. 1 schematically illustrates the combined use, through gas sampling system 10, of an airway adapter 11 and a gas analyzer housing 12. System 10 may be used for insertion directly into a breathing circuit in a non-diverting configuration. The breathing circuit may be configured to communicate with an airway of a subject and may include, but is not limited to, an endotracheal tube, a tracheotomy portal, a tracheotomy tube, a full face mask, a total face mask, a partial rebreathing mask, a nasal cannula and/or other interface appliances that communicate a flow of breathable gas with the airway of a subject. The breathing circuit may be configured to provide a pressurized flow of breathable gas to the airway of the subject (e.g., for mechanical ventilation and/or pressure support therapy), to provide additional oxygen to the airway of the subject, and/or to server other therapeutic purposes. Airway adapter 11 may include input segment 15, output segment 16, an adapter body configured to provide an optical path through airway adapter 11 via window 18, and/or other constituent components.

Airway adapter 11 may be inserted into a breathing circuit, which includes hose 19 and hose 17, by coupling input segment 15 with hose 19 and output segment with hose 17. Gas analyzer housing 12 may include a sensor assembly and may be configured to be removably coupled with airway adapter 11 through adapter interface 20. Adapter interface 20 may allow gas analyzer housing 12 to be snapped on airway adapter 11. Alternatively, and/or simultaneously, operation of adapter interface 20 may be based on matching physical and/or mechanical components including, but not limited to, hooks, clasps, grooves, latches, clamps, clips, buckles, buttons, bolts, screws, fasteners, adhesives, magnets, Velcro, or any combination thereof.

Figure 7A:
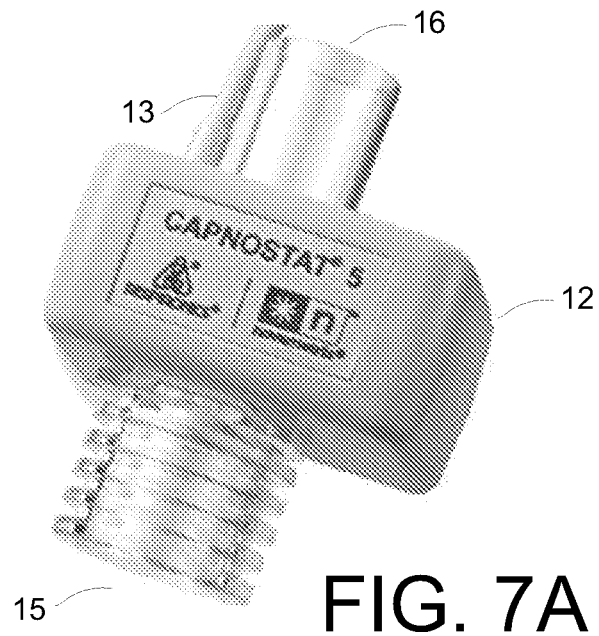
FIG. 7A-7B illustrate embodiments of a gas sampling system.

Gas analyzer housing 12 may be coupled, e.g. via coupling 13, to monitor system 14. Monitor system 14 may be configured to display output signals from a sensor assembly included in gas analyzer housing 12, parameters derived from those output signals, and/or information based on those output signals or derived parameters. Coupling 13 may be wired, wireless, and/or a combination of both. Coupling 13 may include a retractable cable. Power, sensor output data, control input, and/or other information may be exchanged between gas analyzer housing 12 and monitor system 14 over coupling 13. By way of illustration, FIG. 7A illustrates an embodiment of a gas sampling system including an input segment 15, an output segment 16, a coupling 13, and a gas analyzer housing 12 removably coupled with an airway adapter.

Figure 2:
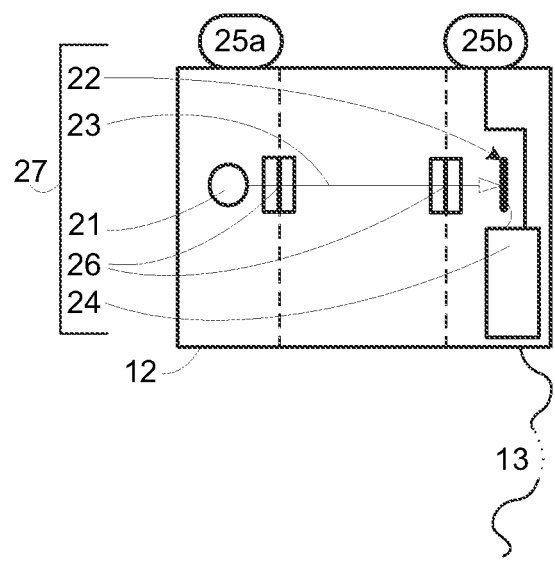
FIG. 2 schematically illustrates a constituent component of a gas sampling system in accordance with one or more embodiments.

FIG. 2 schematically illustrates a constituent component of a gas sampling system in accordance with one or more embodiments. As shown in FIG. 2, gas analyzer housing 12 may include one or more of a sensor assembly 27, a source assembly 21, a detector assembly 22, processing component 24, windows 26, coupling 13, physical interface components 25a and 25b, and/or other constituent components. Sensor assembly 27 may include one or more of source assembly 21, detector assembly 22, processing component 24, windows 26, and/or other constituent components. Source assembly 21 may be configured to pass a beam of radiation 23 through windows 26 to detector assembly 22. Detector assembly 22, in cooperation with processing component 24, may be configured to ascertain the attenuation of the energy in the beam of radiation 23 impinging upon a detector (or sensor) in detector assembly 22. This attenuation may be proportional to the absorption through the gas, by a particular gaseous molecular species, in a particular band of wavelengths. Radiation 23 is intended to pass through a window of an airway adapter, such as window 18 of airway adapter 11, after gas analyzer housing 12 is removably coupled with an airway adapter. Coupling 13 may perform the same function as described in relation to FIG. 1.

In FIG. 2, the illustration of two physical interface components, 25a and 25b, is not meant to be limiting. In certain embodiments, gas analyzer housing 12 may have one physical interface component, or three or more physical interface components. Operation of physical interface components 25a and 25b may be based on matching physical and/or mechanical components including, but not limited to, hooks, clasps, grooves, latches, clamps, clips, buckles, buttons, bolts, screws, fasteners, adhesives, magnets, Velcro, or any combination thereof. Gas analyzer housing 12 may be configured to be used for non-diverting configurations in a manner consistent with the description provided in relation to FIG. 1. Gas analyzer housing 12 may be configured to be used for diverting configurations in a manner described below in relation to FIG. 3.

Figure 3:
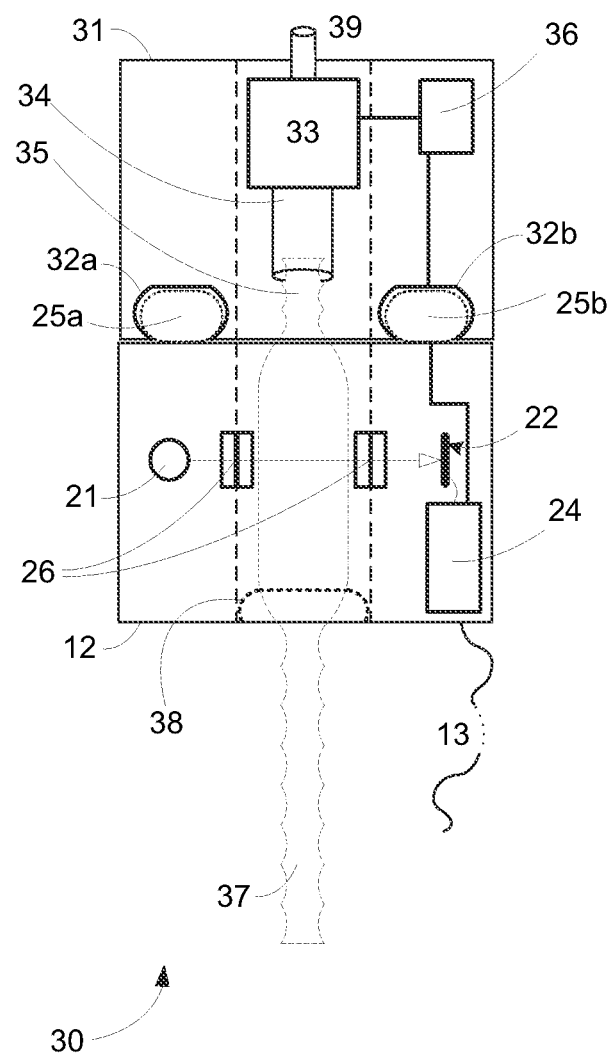
FIG. 3 schematically illustrates a gas sampling system in accordance with one or more embodiments.

FIG. 3 schematically illustrates a gas sampling system in accordance with one or more embodiments. As shown in FIG. 3, gas sampling system 30 may include a gas analyzer housing 12, removably coupled with sidestream component 31, to operate in combination. As described in relation to FIG. 2, gas analyzer housing 12 may include one or more of sensor assembly 27 (not explicitly shown in FIG. 3), source assembly 21, detector assembly 22, coupling 13, processing component 24, windows 26, physical interface components 25a and 25b, and/or other constituent components. In FIG. 3, sidestream component 31 may include one or more of pump 33, pump inlet line 34, processing component 36, sampling cell interface 38, pump interface 39, physical interface components 32a and 32b, and/or other constituent components. For example, for diverting configurations a sampling cell 37 may be removably coupled with gas analyzer housing 12 via sampling cell interface 38. Sampling cell 37 may include a window configured to provide an optical path through sampling cell 37 in alignment with source assembly 21 and detector assembly 22 of gas analyzer housing 12, once coupled. Sampling cell 37 includes a downstream end flange 35 configured to match pump inlet line 34 such that operation of pump 33 moves gas through sampling cell 37. Physical interface components 32a and 32b may be configured to match physical interface components 25a and 25b. Processing component 36 may be configured to control operation of pump 33. Pump interface 39 may be configured to discharge gas from pump 33.

Figure 7B:
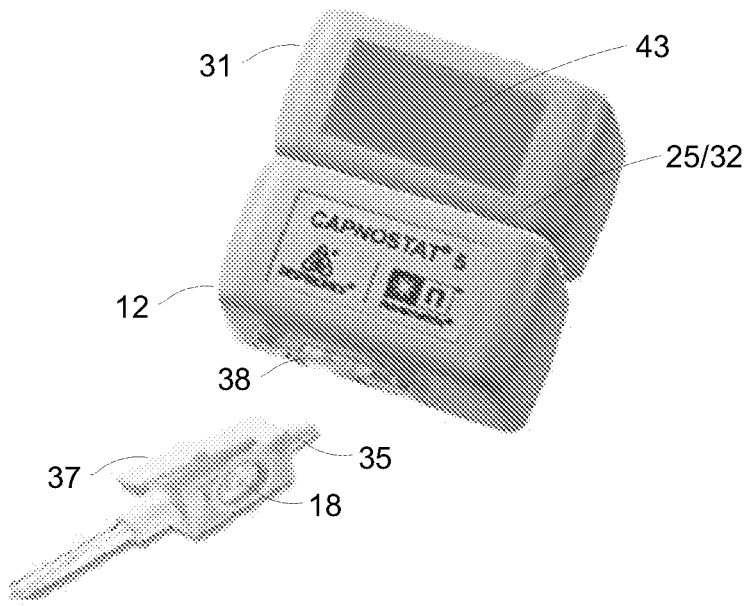

By way of illustration, FIG. 7B illustrates a gas sampling system including a sampling cell 37—having a window 18 and a downstream end flange 35—as well as a gas analyzer housing 12 and a sidestream component 31. Gas analyzer housing 12 in FIG. 7B illustrates sampling cell interface 38 and physical interface component 25. Sidestream component 31 in FIG. 7B illustrates display 43 and physical interface component 32.

In FIG. 3, the physical interface between sidestream component 31 and gas analyzer housing 12 may be operable to allow control and/or communication between processing component 24 and processing component 36. For example, processing component 24 may control pump 33 via processing component 36, or processing component 36 may control operation of source assembly 21 and/or detector assembly 22 via processing component 24. The physical interface may be operable to allow the supply of electrical power from sidestream component 31 to gas analyzer housing 12, and/or vice versa. Transmission of control, communication, and/or electrical power may be accomplished wirelessly, for example through induction, Bluetooth, near field communication, and/or other wireless power and/or information transmission mechanisms or protocols. In certain embodiments, sidestream component 31 and gas analyzer housing 12 may be powered individually.

Power, sensor output data, control input, and/or other information may be exchanged over coupling 13 between gas analyzer housing 12, sidestream component 31, and/or monitor system 14. For example, monitor system 14 may provide electrical power to gas analyzer housing 12, as well as to sidestream component 31 through its physical interface components. Similarly, information originating within sidestream component 31 may be exchanged with monitor system 14 (via gas analyzer housing 12 and/or processed by processing component 24) for presentation to a user of monitor system 14.

Figure 4:
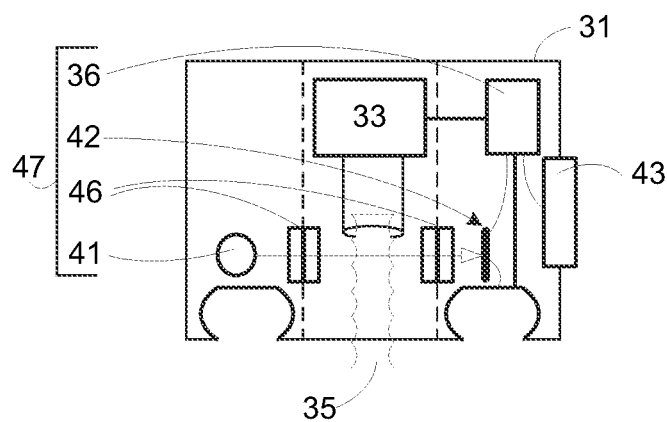
FIG. 4 schematically illustrates a constituent component of a gas sampling system in accordance with one or more embodiments.

FIG. 4 schematically illustrates a constituent component of a gas sampling system in accordance with one or more embodiments. In particular, FIG. 4 illustrates a sidestream component 31 that may include one or more of a sensor assembly 47, a source assembly 41, a detector assembly 42, a display 43, and/or other constituent components, in addition to the components listed in the description of sidestream component 31 related to FIG. 3. In FIG. 4, sensor assembly 47 may include one or more of source assembly 41, detector assembly 42, windows 46, processing component 36, and/or other constituent components. Source assembly 41 and detector assembly 42, in cooperation with processing component 36, may be configured to use the same principles of operation as source assembly 21 and detector assembly 22 of FIG. 2 and FIG. 3, though possibly for a different gaseous molecular species. For example, gas analyzer housing 12 may be used to measure a first set of one or more gaseous molecular species in breathable air, whereas sidestream component 31—in FIG. 4, using sensor assembly 47—may be used to measure one or more other gaseous molecular species or concentrations thereof (e.g., a second set of one or more gaseous molecular species). The illustration in FIG. 4 of sensor assembly 47 as including an optical sensor is not intended to be limiting. Sensor assembly may include, for example, one or more of an infrared gas sensor, a luminescence quenching sensor, a surface acoustic wave sensor, and/or other sensors. The gaseous molecular species may include one or more of oxygen, carbon dioxide, nitrous oxide, propofol and/or other anesthetic agents, and/or other gaseous molecular species or concentrations thereof.

Processing component 36 may be configured to accomplish one or more of the following: control pump 33, cooperate with detector assembly 42, derive parameters from output signals from detector assembly 42, process said parameters and/or output signals to generate presentable information, and/or control display 43 to present one or more of output signals measured/detected by detector assembly 42, derived parameters based on said output signals, and/or generated presentable information. Display 43 may be configured to provide one or more of a representation of output signals from detector assembly 22, a representation of parameters derived from said output signals, and/or information based thereupon, e.g. by communicating through the matching physical interface components of gas analyzer housing 12 and sidestream component 31.

Depending on expected usage, as well as targeted application, a variety of different (mainstream) gas analyzer housings may be removably coupled with a variety of different sidestream components for practical flexibility. The modular approach described herein is designed to combine divertive and non-divertive configurations economically. For example, different sidestream components may include pumps of different quality and/or costs, based on expected levels of use.

Sidestream component 31 may be integrated, embedded, and/or combined with a host monitor, such as monitor system 14, to provide the combined functionality of a sidestream component and a monitor system. Such a system may be configured to provide electrical power to a gas analyzer housing, once coupled.

Figure 5:
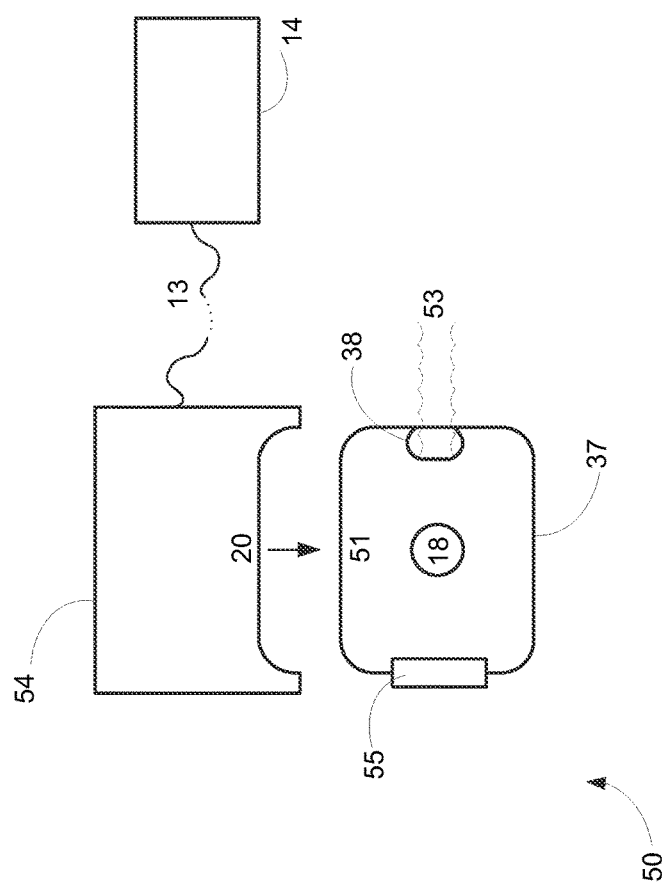
FIG. 5 schematically illustrates a sampling cell in accordance with one or more embodiments.

FIG. 5 schematically illustrates a sampling cell in accordance with one or more embodiments. As used herein, "sampling cell" may refer to a component configured to receive gas for sampling in a diverting configuration. It will be appreciated that in some embodiments, an airway adapter configured for insertion into a breathing circuit in a non-diverting configuration may serve as a sampling cell in a diverting configuration. In other embodiments, such as the embodiment illustrated in FIGS. 5 and 7, the sampling cell is adapted specifically for use in a diverting configuration and a separate airway adapter is used in non-diverting configurations.

Gas sampling system 50 includes one or more of a sampling cell 37, gas analyzer housing 54, coupling 13, and/or monitor system 14. Coupling 13 and monitor system 14 may be configured to provide the same functionality as described in relation to FIG. 1. Gas analyzer housing 54 may be configured to removably couple with sampling cell 37 through adapter 20 of gas analyzer housing 54 and (matching) sampling cell interface 51 of sampling cell 37. Adapter interface 20, together with matching sampling cell interface 51 of sampling cell 37, may allow gas analyzer housing 54 to be snapped on sampling cell 37. Alternatively, and/or simultaneously, the combined operation of adapter interface 20 and sampling cell interface 51 may be based on matching physical and/or mechanical components including, but not limited to, hooks, clasps, grooves, latches, clamps, clips, buckles, buttons, bolts, screws, fasteners, adhesives, magnets, Velcro, or any combination thereof.

Gas analyzer housing 54 may include a sensor assembly, a source assembly, a detector assembly, and a processing component that operate substantially the same as the respective components in gas analyzer housing 12 (in FIG. 2). Sampling cell 37 may include a window 18 configured to provide an optical path through sampling cell 37, such that the optical path is available for use by a sensor assembly of gas analyzer housing 54, once coupled. Sampling cell 37 may include a sampling cell interface 38 configured to removably couple with a sampling line 53. Sampling cell 37 may include an exhaust/pump interface 55 configured to removably couple with a pump in a first mode of operation such that operation of the pump moves gas through sampling cell 37, and furthermore configured to discharge gas from sampling cell 37 in a second mode of operation. The first mode and second mode of operation may correspond to diverting and non-diverting configurations, respectively.

Referring back to FIG. 7B, sampling cell 37 is depicted as being separate from sampling cell interface 38. It will be appreciated that this is not intended to be limiting. In some embodiments, sampling cell interface 38 and sampling cell 37 are formed as an individual component, and the sampling line may removably interface with sampling cell 37.

Figure 6:
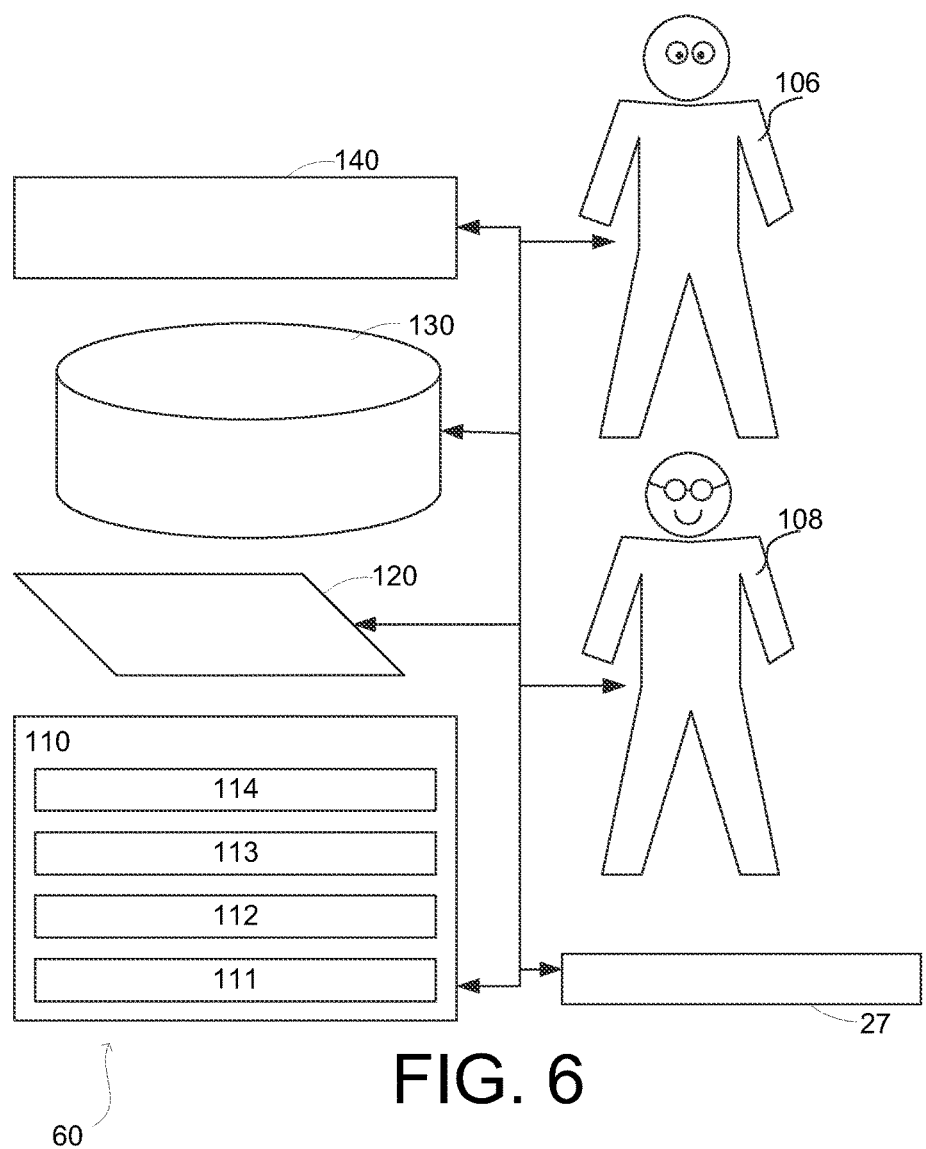
FIG. 6 schematically illustrates a gas sampling system according to one or more embodiments.

FIG. 6 schematically illustrates a gas sampling system 60 according to one or more embodiments. Gas sampling system 60 may include a sensor assembly 27, processor 110, user interface 120, electronic storage 130, a power supply/power interface 140, and/or other components. Gas sampling system 60 may interact with subject 106, user 108, and/or other subjects.

Gas sampling system 60 may include power supply/power interface 140 configured to supply electrical power to constituent components of gas sampling system 60, as well as external components coupled with gas sampling system 60 through physical interface components akin to physical interface component 25a and 25b as described in relation to FIG. 3. Power supply/power interface 140 may include one or more of a battery, a power plug, a power cable, and/or other ways to transfer electrical power into gas sampling system 60.

Gas sampling system 60 may include electronic storage 130 comprising electronic storage media that electronically stores information. The electronic storage media of electronic storage 130 includes one or both of system storage that is provided integrally (i.e., substantially non-removable) with gas sampling system 60 and/or removable storage that is removably connectable to gas sampling system 60 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 130 stores software algorithms, information determined by processor 110, information received via user interface 120, and/or other information that enables gas sampling system 60 to function properly. For example, electronic storage 130 may record or store one or more parameters derived from output signals measured by a sensor assembly (as discussed elsewhere herein), and/or other information. Electronic storage 130 may be a separate component within gas sampling system 60, or electronic storage 130 may be provided integrally with one or more other components of gas sampling system 60 (e.g., processor 110).

Gas sampling system 60 may include user interface 120 configured to provide an interface between gas sampling system 60 and a user (e.g., user 108, subject 106, a caregiver, a therapy decision-maker, etc.) through which the user can provide information to and receive information from gas sampling system 60. This enables data, results, and/or instructions and any other communicable items, collectively referred to as "information," to be communicated between the user and gas sampling system 60. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information is e.g. provided to subject 106 by user interface 120 in the form of auditory signals, visual signals, tactile signals, and/or other sensory signals.

By way of non-limiting example, in certain embodiments, user interface 120 includes a radiation source capable of emitting light. The radiation source includes one or more of an LED, a light bulb, a display screen, and/or other sources. User interface 120 may control the radiation source to emit light in a manner that conveys to subject 106 information related to, e.g., the operation of the sensor assembly. Note that the subject and the user of gas sampling system 60 may be the same person.

It is to be understood that other communication techniques, either hard-wired or wireless, are also contemplated herein as user interface 120. For example, in one embodiment, user interface 120 is integrated with a removable storage interface provided by electronic storage 130. In this example, information is loaded into gas sampling system 60 from removable storage (e.g., a smart card, a flash drive, a removable disk, etc.) that enables the user(s) to customize the implementation of gas sampling system 60. Other exemplary input devices and techniques adapted for use with gas sampling system 60 as user interface 120 include, but are not limited to, an RS-232 port, RF link, an IR link, modem (telephone, cable, Ethernet, internet or other). In short, any technique for communicating information with gas sampling system 60 is contemplated as user interface 120.

Processor 110 is configured to provide information processing capabilities in gas sampling system 60. As such, processor 110 includes one or more of a digital processor, an analog processor, a digital circuit designed to process information, an analog circuit designed to process information, a state machine, and/or other mechanisms for electronically processing information. Although processor 110 is shown in FIG. 6 as a single entity, this is for illustrative purposes only. In some implementations, processor 110 includes a plurality of processing units.

As is shown in FIG. 6, processor 110 is configured to execute one or more computer program modules. The one or more computer program modules include one or more of a source assembly control module 111, a detector assembly control module 112, an interface control module 113, a pump control module 114, and/or other modules. Processor 110 may be configured to execute modules 111, 112, 113, and/or 114 by software; hardware; firmware; some combination of software, hardware, and/or firmware; and/or other mechanisms for configuring processing capabilities on processor 110.

It should be appreciated that although modules 111, 112, 113, and 114 are illustrated in FIG. 1 as being co-located within a single processing unit, in implementations in which processor 110 includes multiple processing units, one or more of modules 111, 112, 113, and/or 114 may be located remotely from the other modules. The description of the functionality provided by the different modules 111, 112, 113, and/or 114 described below is for illustrative purposes, and is not intended to be limiting, as any of modules 111, 112, 113, and/or 114 may provide more or less functionality than is described. For example, one or more of modules 111, 112, 113, and/or 114 may be eliminated, and some or all of its functionality may be provided by other ones of modules 111, 112, 113, and/or 114. Note that processor 110 may be configured to execute one or more additional modules that may perform some or all of the functionality attributed below to one of modules 111, 112, 113, and/or 114.

Source assembly control module 111 may be configured to control source assembly 21 and/or control emission of radiation from source assembly 21, e.g. beam of radiation 23 as described in relation to FIG. 2. Source assembly control module 111 may control the level of energy in radiation 23, and/or any characteristics pertaining to the shape, intensity, duration, pulse-length, frequency, wavelength, or other characteristics of radiation 23.

Detector assembly control module 112 may be configured to control detector assembly 22. Detector assembly 22, in cooperation with a detector assembly control module 112, may be configured to ascertain the attenuation of the energy in a beam of radiation originating from source assembly 21 and impinging upon a detector (or sensor) in detector assembly 22. This attenuation may be proportional to the absorption through a gas, by a particular gaseous molecular species, in a particular band of wavelengths. Output signals from detector assembly 22 may be used to derive parameters and/or information based on said output signals and/or on derived parameters.

Interface control module 113 may be configured to control the transfer of communication signals, control signals, and/or power across physical interface components. For example, if a sidestream component is coupled with gas sampling system 60, interface control module 113 may control the supply of electrical power via the power supply/power interface 140.

Pump control module 114 may be configured to control the operation of a pump, either in a coupled sidestream component or in gas sampling system 60. In the former case, pump control signals may transfer across a physical interface component to the pump of a sidestream component. Some or all of the functionality of any computer program module described herein may be incorporated or integrated into other computer program modules of processor 110.

Figure 8A:
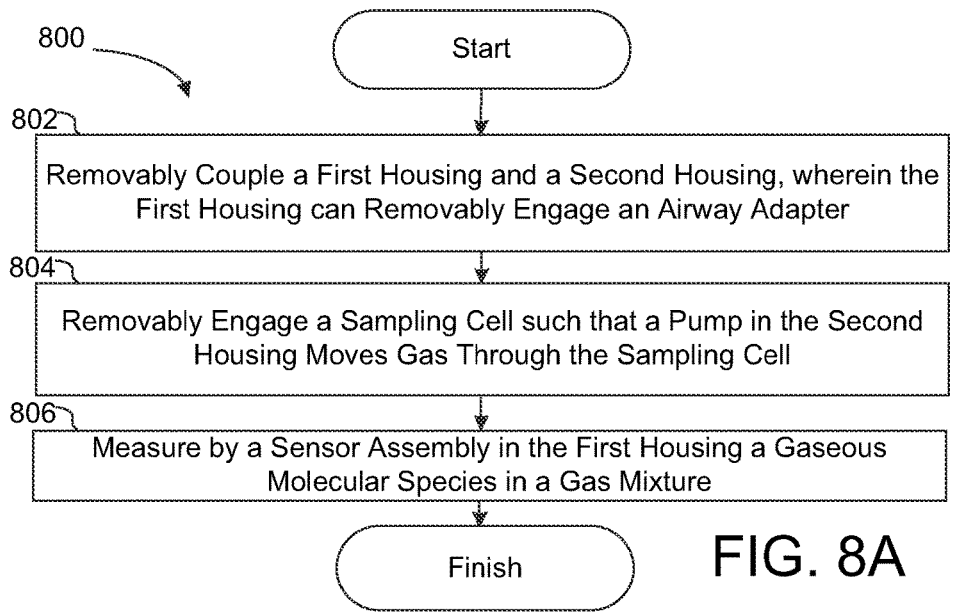
FIG. 8A-8B illustrate methods for analyzing a gas.
Figure 8B:
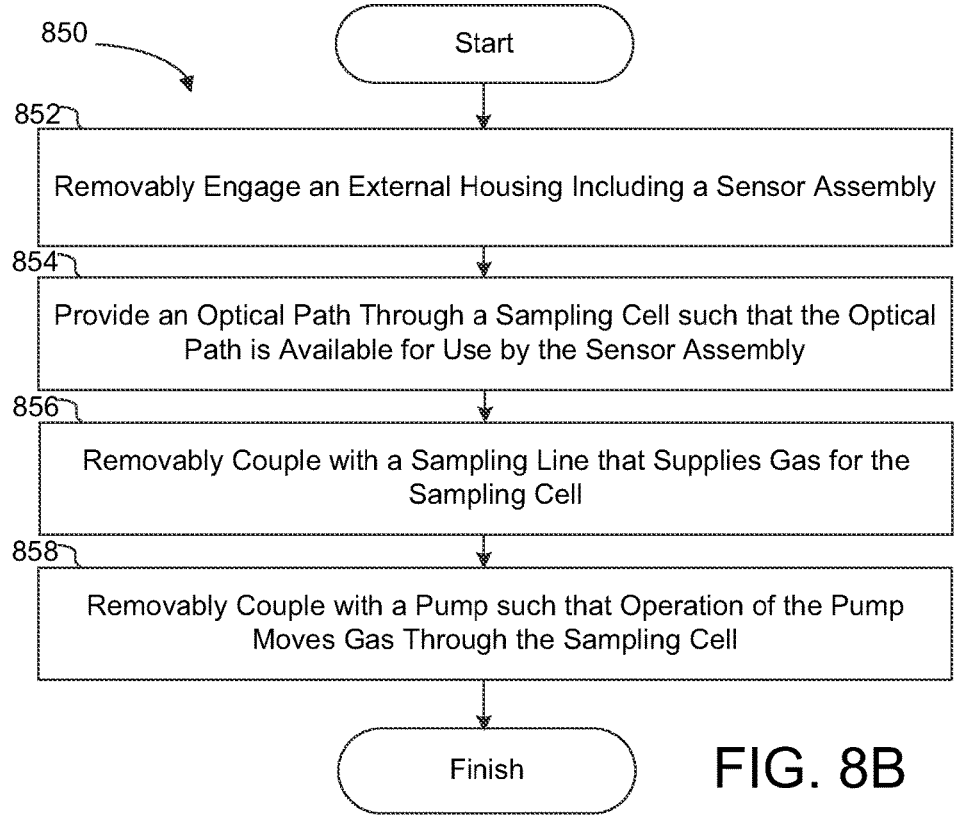

FIGS. 8A and 8B illustrate methods 800 and 850 for operating a gas sampling system. The operations of methods 800 and 850 presented below are intended to be illustrative. In certain embodiments, methods 800 and 850 may be accomplished with one or more additional operations not described, and/or without one or more of the operations discussed. Additionally, the order in which the operations of methods 800 and 850 are illustrated in FIG. 3 and described below is not intended to be limiting.

In certain embodiments, methods 800 and 850 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of methods 800 and 850 in response to instructions stored electronically on an electronic storage medium. The one or more processing devices may include one or more devices configured through hardware, firmware, and/or software to be specifically designed for execution of one or more of the operations of methods 800 and 850.

At an operation 802, a first housing is removably coupled with a second housing, wherein the first housing can removably engage an airway adapter. In one embodiment, operation 802 is performed using a gas analyzer housing and a pump housing similar to or substantially the same as gas analyzer housing 12 and sidestream component 31 (shown in FIG. 3 and described above).

At an operation 804, a sampling cell is removably engaged such that gas within the sampling cell is measured by a sensor assembly, and operation of a pump in the second housing moves gas through the sampling cell. In one embodiment, operation 804 is performed using a sampling cell interface similar to or substantially the same as sampling cell interface 38 (shown in FIG. 3 and described above).

At an operation 806, a gaseous molecular species is by measured in a gas mixture by a sensor assembly in the first housing. In one embodiment operation 806 is performed by a sensor assembly similar to or substantially the same as sensor assembly 27 (shown in FIG. 2 and described above).

Regarding method 850, at an operation 852, an external housing including a sensor assembly is removably engaged. In one embodiment, operation 852 is performed by a sampling cell similar to or substantially the same as sampling cell 37 (shown in FIG. 5 and described above).

At an operation 854, an optical path is provided through the sampling cell such that the optical path is available for use by a sensor assembly, once coupled with a gas analyzer housing. In one embodiment, operation 854 is performed by a window similar to or substantially the same as window 18 (shown in FIG. 5 and described above).

At an operation 856, gas is supplied by removably coupling with a sampling line configured to supply gas for sampling via the sampling cell. In one embodiment, operation 856 is performed by a sampling line similar to or substantially the same as sampling line 53 (shown in FIG. 5 and described above).

At an operation 858, a pump is removably coupled such that operation of the pump moves gas through the sampling cell. In one embodiment, operation 858 is performed by an exhaust/pump interface similar to or substantially the same as exhaust/pump interface 55 (shown in FIG. 5 and described above).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the embodiments have been described in detail for the purpose of illustration based on what is currently considered to be most practical and preferred, it is to be understood that such detail is solely for that purpose and that no limitations to the disclosed embodiments are intended. On the contrary, the claims are intended to cover modifications and equivalent arrangements that are within the spirit and scope of the disclosure. For example, it is to be understood that the present disclosure contemplates that, to the extent possible, one or more features of any embodiment can be combined with one or more features of any other embodiment.

What is claimed is:

1. A gas sampling system comprising:
   a first housing comprising a sensor assembly, wherein the sensor assembly is configured to measure a gaseous molecular species in a gas mixture, and wherein the first housing is configured to removably engage an airway adapter configured for insertion into a breathing circuit in fluid communication with a subject, and further comprising on an outer surface of the first housing, a first physical interface component and a second physical interface component; and
   a second housing comprising a pump, a pump inlet configured to reversibly receive a portion of the airway adapter, a pump outlet, and further comprising, formed in an outer surface of the second housing, a first physical interface component complementary to the first physical interface component of the first housing, and a second physical interface component complementary to the second physical interface component of the first housing, wherein the first housing and the second housing are further configured to removably couple with each other via the physical interface components such that a processing component in the first housing is configured to control operation of the pump in the second housing, wherein at least one set of complementary physical interface components are configured such that the processing component in the first housing is in wired communication with the pump of the second housing via the at least one set of complementary physical interface components;
   wherein the first and second housings are configured to engage the airway adapter such that operation of the pump in the second housing pulls gas into the first housing where the gas is measured by the sensor assembly, and then into the second housing via the pump inlet, and wherein the second housing is configured to exhaust the measured gas via the pump outlet of the second housing.

2. The gas sampling system of claim 1, wherein the second housing further includes one selected from the group consisting of (i) a second sensor assembly, (ii) a display, and (iii) both a second sensor assembly and a display.

3. The gas sampling system of claim 1, wherein the physical interface components are further configured such that the first housing provides an electrical power interface to the second housing.

4. A method of analyzing a gas, the method comprising;
   removably coupling a first housing comprising a sensor assembly and a processing component to a second housing comprising a pump and a pump inlet configured to reversibly receive a portion of an airway adapter, wherein the sensor assembly is configured to measure a gaseous molecular species in a gas mixture, and further wherein the first housing is further configured to removably engage an airway adapter configured for insertion into a breathing circuit in fluid communication with a subject, wherein the outer surface of the first housing comprises a first physical interface component and a second physical interface component, and further wherein a first physical interface component is formed in an outer surface of the second housing complementary to the first physical interface component of the first housing, and further wherein a second physical interface component is formed in an outer surface of the second housing complementary to the second physical interface component of the first housing, wherein the first housing and the second housing are configured to removably couple with each other via the physical interface components, wherein at least one set of complementary physical interface components are configured such that the processing component in the first housing is in wired communication with the pump of the second housing via the at least one set of complementary physical interface components;
   removably engaging the airway adapter, via the first and second housings, such that operation of the pump in the second housing pulls gas from the airway adapter into the first housing and then into the second housing via the pump inlet, wherein operation of the pump is controlled by the processing component of the first housing;
   measuring, by the sensor assembly, a gaseous molecular species in the gas pulled into the first housing; and
   exhausting, via an exhaust of the second housing, the measured gas.

5. The method of claim 4, wherein the second housing further includes a display, further comprising providing a representation of a measurement by the sensor assembly via the display.

6. The method of 4, wherein the first housing provides an electrical power interface to the second housing.

7. A method of analyzing a gas, the method comprising:
   removably engaging an external housing with a sampling cell, the external housing comprising a sensor assembly configured to measure a gaseous molecular species in a gas mixture, and further comprising in an outer surface of the external housing a first physical interface component and a second physical interface component, and further wherein a first physical interface component is formed in an outer surface of the sampling cell to the first physical interface component of the first housing;
   providing an optical path through the sampling cell such that the optical path is available for measurements by the sensor assembly;
   removably coupling the sampling cell with a sampling line, wherein the sampling line is configured to supply gas for measurements by the sensor assembly;
   removably coupling the external housing with a second housing, wherein a first physical interface is formed in an outer surface of the second housing complementary to the first physical interface component of the first housing, and a second physical interface is formed in an outer surface of the second housing complementary to the second physical interface component of the first housing, wherein at least one set of complementary physical interface components are configured such that the processing component in the first housing is in wired communication with the pump of the second housing via the at least one set of complementary physical interface components;

wherein the external housing further comprises a processing component and the second housing comprises a pump such that operation of the pump, controlled by the processing component in the external housing, moves gas through the sampling cell;

and measuring, by the sensor assembly, a gaseous molecular species in the gas pulled info the first housing.

8. A system configured to analyze a gas, the system comprising:

first means for measuring a gaseous molecular species in a gas mixture;

second means for housing the first means, wherein the second means is configured to removably engage an airway adapter configured for insertion into a breathing circuit in fluid communication with a subject, wherein the outer surface of the second means comprises a first physical interface component and a second physical interface component;

third means for housing a pump and comprising a pump inlet configured to reversibly receive a portion of the airway adapter, wherein the third means comprises a first physical interface component formed in an outer surface and complementary to the first physical interface component of the second means, and wherein the third means further comprises a second physical interface component formed in the outer surface and complementary to the second physical interface component of the second means, wherein the second means and third means are configured to removably couple with each other via the physical interface components, wherein at least one set of complementary physical interface components are configured such that the processing component in the second means is in wired communication with the pump of the third means via the at least one set of complementary physical interface components, wherein the second means further houses a processing component configured to control operation of the pump in the third means; and fourth means for removably engaging a sampling cell such that gas within the sampling cell is analyzed by the first means, and such that operation of the pump pulls gas from the airway adapter into the first means.

9. The system of claim 8, further comprising:

fifth means for providing a representation of a measurement by the first means.

10. The system of claim 8, wherein the second means includes sixth means for processing, and wherein the physical interface components are further configured such that the second means provides an electrical power interface to the third means.

* * * * *